(12) United States Patent
Randolph

(10) Patent No.: US 6,767,334 B1
(45) Date of Patent: Jul. 27, 2004

(54) METHOD AND APPARATUS FOR WOUND TREATMENT

(75) Inventor: L. Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 09/830,280

(22) PCT Filed: Dec. 23, 1999

(86) PCT No.: PCT/US99/30702

§ 371 (c)(1),
(2), (4) Date: Apr. 3, 2001

(87) PCT Pub. No.: WO00/38755

PCT Pub. Date: Jul. 6, 2000

Related U.S. Application Data

(60) Provisional application No. 60/113,732, filed on Dec. 23, 1998.

(51) Int. Cl.[7] .......................... A61M 1/00; A61M 35/00; A61M 27/00; A61F 13/00

(52) U.S. Cl. .......................... 604/35; 604/290; 604/543; 602/42

(58) Field of Search ........................... 604/28, 35, 290, 604/540–544; 602/41–43, 46, 47

(56) References Cited

U.S. PATENT DOCUMENTS

| 1,114,268 A | * | 10/1914 | Kells ........................... 604/171 |
| 4,421,505 A | * | 12/1983 | Schwartz ....................... 604/28 |
| 5,636,643 A | * | 6/1997 | Argenta et al. ............. 128/897 |

* cited by examiner

*Primary Examiner*—Michael J. Hayes

(57) ABSTRACT

A wound treatment device comprises a polyurethane or polyether foam pad, adapted for insertion substantially within a wound cavity; a pump for supplying fluid flow to the wound site; and a collection canister for receiving wound fluids drawn from the wound cavity. The foam pad, pump and collection canister are in fluid communication with one another through a single hospital grade hose having a plurality of tiny apertures in the portion that is central to the foam pad. These apertures are adapted to allow fluids from the wound cavity to be drawn into the flow from the pump to the canister according to Bernoulli's theorem.

9 Claims, 1 Drawing Sheet

METHOD AND APPARATUS FOR WOUND TREATMENT

RELATED APPLICATIONS

This application is a continuation of International Application No. PCT/US99/30702 entitled METHOD AND APPARATUS FOR WOUND TREATMENT filed Dec. 23, 1999, now abandoned, which claimed priority to U.S. Provisional Patent Application Serial No. 60/113,732 entitled METHOD AND APPARATUS FOR WOUND TREATMENT filed Dec. 23, 1998. By this reference, the full disclosures, including the drawings, of U.S. Provisional Patent Application Serial No. 60/113,732 and International Application No. PCT/US99/30702 are incorporated herein.

TECHNICAL FIELD

The present invention relates to the treatment of wounds. More particularly, the invention relates to the therapeutic application of a positive fluid flow to a wound site for the promotion of wound healing.

BACKGROUND ART

It is known in the prior art that wound closure requires that the epithelial and subcutaneous tissues adjacent the wound migrate toward the wound. Unfortunately, in the case of large or infected wounds, often the result of chronic disease or pressure sores, spontaneous closure does not take place. In these cases, localized swelling forms near the surface of the wound restricting flow of blood. As a result of this diminished blood flow the wound is unable to successfully fight bacterial infection. The resulting increased infection causes further restriction of blood flow, which in turn results in further diminished blood flow and so forth, ultimately leading to the necessity for radical intervention. In many cases the patient requires hospitalization for drug administration and/or surgical treatment.

The application of continuous negative pressure has been shown to contribute significantly to wound closure. Such applications typically involve the insertion of an open cell foam pad into a wound region. The pad is then covered with a polymer sheet to seal the region from atmosphere. Thereafter, negative pressure is applied to the wound site through a tube having one end inserted into the interior of the foam pad and the opposite end attached to a vacuum pump via an interposed chamber for collection of wound fluids. Clinical results demonstrate that such applications of negative pressure promote the migration of epithelial and subcutaneous tissue toward the wound while serving to evacuate wound exudates and reduce bacterial density.

Unfortunately, the application of continuous negative pressure makes difficult the administration of topical disinfectant drugs and control of the local atmospheric content and does little to promote drying of the wound area. It is therefore desired to achieve infection control in a manner that promotes the application of topical disinfectants while allowing the caregiver to adjust the local atmospheric condition, including content and temperature. The removal of wound fluids through continuous negative pressure also suffers the disadvantage of requiring strict infection control. This is most often accomplished through the provision of very expensive hydrophobic filters between the collection canister and vacuum pump and other safety measures. It is therefore desirable to eliminate the necessity for such expensive apparatuses while still providing a safe and effective means for the removal of wound exudates.

In accordance with the foregoing objects, the present invention—a method and apparatus for wound treatment—generally comprises a polyurethane or polyether foam pad, adapted for insertion substantially within a wound cavity; a pump for supplying fluid flow to the wound site; and a collection canister for receiving wound fluids drawn from the wound cavity. The foam pad, pump and collection canister are in fluid communication with one another through a single hospital grade hose having a plurality of tiny apertures in the portion that is central to the foam pad. These apertures are adapted to allow fluids from the wound cavity to be drawn into the flow from the pump to the canister according to Bernoulli's theorem, which states generally that the work done on a fluid is equal to the change in kinetic energy of the fluid.

Many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

Figure 1:
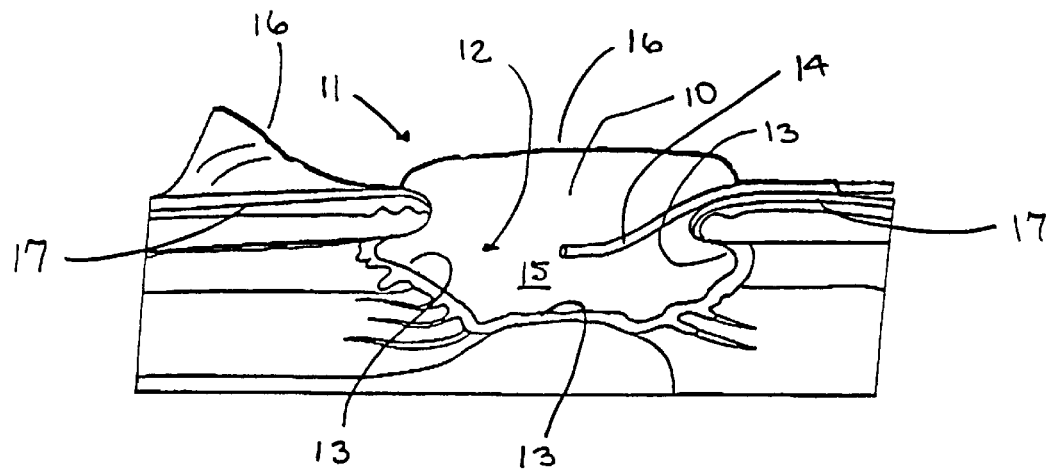
FIG. 1 shows a partial cross section of a known apparatus for application of continuous negative pressure to a wound site.

Referring to FIG. 1, there is shown a partial cross-sectional view of an open cell polyurethane or polyether foam pad 10 as inserted into a wound site 11 for application of continuous negative pressure as previously known in the art. As detailed in the figure, the foam pad 10 is cut top size so as to pack the foam 10 into the wound cavity 12, making contact with the full surface 13 of the cavity 12. A drainage tube 14, preferably comprising medical grade polyvinyl chloride (PVC), is terminated within the central portion 15 of the foam pad 10 and the pad 10 and tube 14 combination is covered with a surgical drape 16. The drape 16 is preferably adhered firmly to the intact skin 17 peripheral the wound site 11 as well as to the drainage tube 14 in order to provide an airtight seal around the wound 11. Negative pressure is then applied through the drainage tube 14 utilizing known apparatus not shown here.

Figure 2:
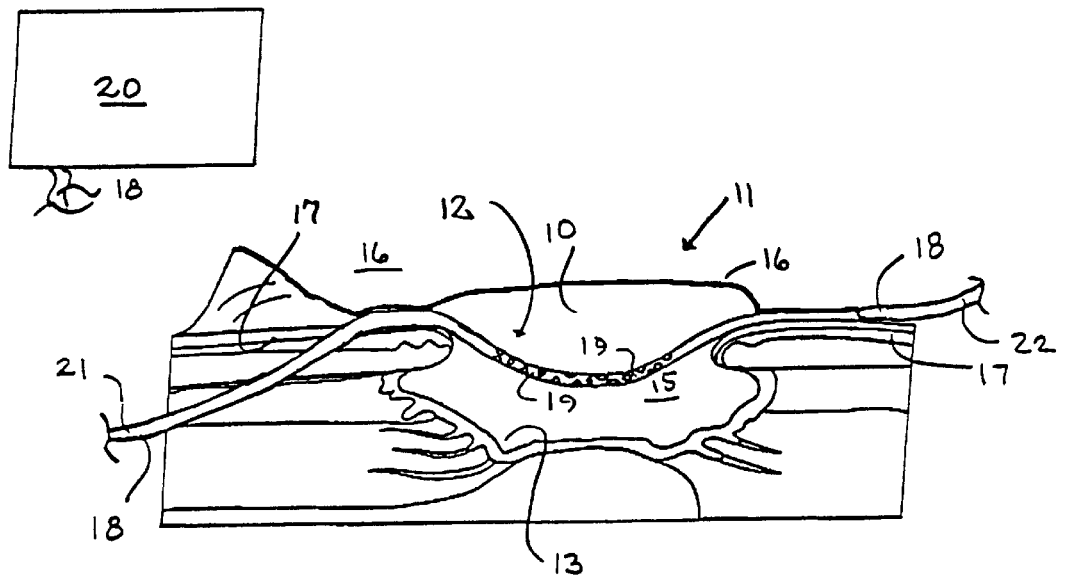
FIG. 2 shows a partial cross section of a preferred embodiment of the present invention as applied to a wound site, including in block diagram the pump and collection canister forming a part thereof.
Figure 2:
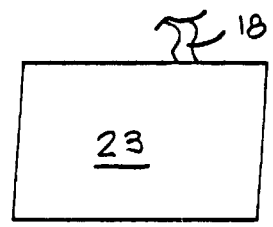

Referring now to FIG. 2, there is shown a partial cross-sectional view of an open cell-polyurethane or polyether foam pad 10 as inserted into a wound site 11 for application of positive pressure according to the teachings of the present invention. While the present invention employs many principles known from the art of negative pressure applications for wound site preparation, material selection, and even therapeutic modality, the present invention varies from the known art in several critical areas. First, the present invention is adapted to apply a positive pressure to the wound site 11. As shown in the figure, the PVC tube 18 providing fluid communication both to and from the inserted pad 10 comprises a plurality of tiny apertures 19 in the region 15 central to the pad 10. Positive pressure, preferably generated with a non-oil type clean air delivery pump 20 meeting applicable hospital standards such as UL-544, is delivered to a first end 21 of the tube. By varying the temperature and flow rate of the fluid delivered to the wound site 11 through the tube 18 and provided apertures 19, the caregiver is given the ability to control the drying characteristics of the fluid. Additionally, the caregiver can vary the content of the fluid in order to promote increased healing. For example, the pump 20 may be adapted to deliver pure $O_2$ for a localized hyperbaric effect or $O_3$ for ozone treatment and infection controlling drugs may be easily admitted into the flow stream for topical administration to the wound 11.

In addition, the placement of the tiny apertures 19 in the flow stream relative to the second, or drainage, end 22 of the tube 18 creates a venturi. As is generally Known in the relevant arts, a venture operates through the Bernoulli effect to create a relative low pressure in areas of increased fluid flow rate in a closed or semi-closed system. According the present invention, the drainage end 22 of the tube 18 is connected to fluid collection canister 23 wherein the local pressure is controlled to ensure establishment of the desired venture. In this manner, a localized suction is created at the wound site 11, notwithstanding the fact that the pressure at the wound 11 will be greater than that of the surrounding atmosphere, whereby wound exudates may be safely drawn from the wound 11. This helps to eliminate moisture buildup at the wound site 11 and reduces bacterial density, thereby aiding in the control of infection and assisting in the control of edema.

As an additional benefit, the system of the present invention eliminates the need for many of the more expensive elements of infection control. For example, because the collection canister 23 is at the terminal end of the pressure delivery apparatus, the requirements for hydrophobic filtering and strict contamination monitoring are reduced or eliminated. This makes the apparatus of the present invention available at far more economical rates, while maintaining patient safety standards intact.

While the foregoing description is exemplary of the preferred embodiment of the present invention, those of ordinary skill in the relevant arts will recognize the many variations, alterations, modifications, substitutions and the like as are readily possible, especially in light of this description and the accompanying drawings and claims drawn hereto. In any case, because the scope of the present invention is much broader than any particular embodiment, the foregoing detailed description should not be construed as a limitation of the scope of the present invention, which is limited only by the claims that may be drawn hereto.

What is claimed is:

1. An apparatus for the promotion of wound closure, said apparatus comprising:
    a pad adapted for insertion substantially within a wound cavity;
    a pump adapted to pump fluid away from said pump;
    a reservoir adapted for collection of wound fluids;
    a fluid conduit adapted for conveying said fluid from said pump, then through said pad and to said reservoir; and
    a venturi communicating with said fluid conduit and positioned adjacent said pad to create a suction at said pad and within the wound cavity;
    wherein the pump is positioned at a first end of said fluid conduit.

2. The apparatus as recited in claim 1, wherein said venturi is comprised of a plurality of tiny apertures.

3. The apparatus as recited in claim 2, wherein said apertures are enveloped within said pad.

4. The apparatus as recited in claim 1, wherein said fluid conduit comprises a tube.

5. The apparatus as recited in claim 1, further comprising an adaptation for the introduction to said fluid flow of an infection controlling drug.

6. The apparatus as recited in claim 1, wherein said reservoir is positioned at a terminal end of said apparatus, and wherein said pad within said wound cavity is positioned between said terminal end and said pump.

7. The apparatus as recited in claim 1, further comprising a drape covering said pad and adhered to intact skin peripheral the wound cavity.

8. The apparatus as recited in claim 7, wherein said drape forms an airtight seal around the wound cavity.

9. A method for the promotion of wound closure, said method comprising the steps of:
    inserting a pad substantially within a wound cavity;
    providing a fluid conduit;
    providing a reservoir for collection of wound fluids at a terminal end of said fluid conduit;
    forming an airtight seal over said pad and the wound cavity with a drape;
    providing a pump at a first end of said fluid conduit for conveying fluid flow away from said pump through said fluid conduit then through said pad and to said reservoir; and
    providing a venturi within a region of said fluid conduit adjacent said pad such that a negative pressure is created at the wound site as fluid passes through said fluid conduit.

* * * * *